United States Patent [19]

Satoh et al.

[11] Patent Number: 4,757,007
[45] Date of Patent: Jul. 12, 1988

[54] PROCESS FOR PREPARING HYDROLYZED PRODUCTS OF SOY PROTEIN

[75] Inventors: Masaaki Satoh; Yukio Matsumoto; Koji Hasegawa; Gyota Taguchi; Hiroshi Mimoto, all of Yokohama, Japan

[73] Assignee: The Nisshin Oil Mills, Ltd., Tokyo, Japan

[21] Appl. No.: 704,693

[22] Filed: Feb. 22, 1985

[30] Foreign Application Priority Data

Feb. 22, 1984 [JP] Japan ................. 59-30396

[51] Int. Cl.$^4$ ............................................. C07K 3/12
[52] U.S. Cl. ..................................... 435/69; 435/272; 530/378; 210/632; 210/634; 210/639; 426/46
[58] Field of Search ............... 435/68, 69, 212–226, 435/262, 267, 272, 803; 514/2; 530/300, 343, 344, 350, 370, 377, 378, 412, 414, 418; 47/58; 210/632, 634, 639, 640, 702, 724, 737, 767; 426/46, 49, 52, 44, 63, 604, 570–573, 605, 654, 656, 802, 803

[56] References Cited

U.S. PATENT DOCUMENTS

| | | | |
|---|---|---|---|
| 2,489,208 | 5/1945 | Turner | 426/46 |
| 3,966,985 | 6/1976 | Jonas | 426/533 |
| 4,015,019 | 3/1977 | Sawada | 426/46 |
| 4,302,474 | 11/1981 | Mikami | 426/52 |
| 4,304,795 | 12/1981 | Takada | 426/602 |
| 4,343,825 | 8/1982 | Takada | 426/570 |
| 4,426,395 | 1/1984 | Sakai | 426/46 |
| 4,431,629 | 2/1984 | Olsen | 426/46 |
| 4,477,472 | 10/1984 | Seto | 426/98 |

OTHER PUBLICATIONS

Biosis Abstract 84;346675; Kamata, Y. et al., Agricul. Biol. Chem. 48 (5): 1147–1152 (1984).
Biosis Abstract 81:259,985; Jenkins, K. et al., Can. J. Anim. Sci., 60 (4): 907–914 (1980).
Biosis Abstract 81:283519; Do Prado, V. C. et al., Arch. Latinoam. Nutr., 30 (4): 552–563 (1980).
Biosis Abstract 78:208538; Zakaria, F. et al., –Lebenom Wiss Technol. 11(1): 42–44 (1978).

Primary Examiner—Margaret Moskowitz
Attorney, Agent, or Firm—Sughrue, Mion, Zinn, Macpeak, and Seas

[57] ABSTRACT

Two kinds of hydrolyzed protein having different characteristics respectively are obtained by hydrolyzing soy protein with protease and separating the mixture of hydrolyzed products using their solubilities in a 5% trichloro acetic acid aqueous solution as the guidance of the separation.

The hydrolyzed protein of the low solubility possesses excellent emulsifying properties, and the one of the high solubility possesses excellent foaming properties.

18 Claims, No Drawings

PROCESS FOR PREPARING HYDROLYZED
PRODUCTS OF SOY PROTEIN

BACKGROUND OF THE INVENTION (1) Field of the Invention

This invention relates to a process for preparing two kinds of hydrolyzed products of soy protein by separating the products after partially hydrolyzing soy protein with a protease.

One such product possesses excellent foaming properties, and the other possesses excellent emulsifying properties.

(2) Description of the Prior Art

Up to the present, it is known that the emulsifying properties or foaming properties of soy protein are improved by hydrolyzing it partially with protease (see "Studies on enzyme modified proteins as foaming agents: Effect of structure on foam stability" T. Horiuchi et al., Food Chem., 3, 35(1978); "Studies on the emulsifying properties of soybean proteins: Part II. Effect of partial hydrolysis" H. Aoki et al., Nippon Shokuhin Kogyo Gakkaishi, 23, 26(1976); and "Modification of functional properties of soy proteins by proteolytic enzyme treatment", G. Puski, Cereal Chem., 52, 655(1975)).

But a process that is able to prepare simultaneously a foaming agent and an emulsifying agent by hydrolyzing soy protein with protease and separating the hydrolyzed products subsequently has not been found yet.

SUMMARY OF THE INVENTION

It has been found that both the hydrolyzed protein possessing emulsifying properties and the other hydrolyzed protein possessing foaming properties can be obtained simultaneously from the hydrolyzed products by using the solubility of them by 5% aqueous solution of trichloroacetic acid (hereinafter referred to as "a 5% TCA solubilization by weight") as the guidance of separation.

In accordance with this invention, there is provided a process for the preparation of hydrolyzed products of soy protein which comprises partially hydrolyzing soy protein with protease, then separating the resulting hydrolyzed products by using the 5% TCA solubilization by weight into two parts wherein one part has a solubilization of 10–40% by weight and the other part has a solubilization of 70% or more by weight. The former is useful for emulsifying agent, and the latter is useful for foaming agent.

DETAILED DESCRIPTION OF THE INVENTION

In accordance with this invention, protein of soybean is used for raw material. Soy proteins treated by heat or with alcohol are used for increasing the efficiency of hydrolysis and/or for improving the flavor of the final products.

As the protease being used for hydrolysis in accordance with this invention, there can be employed, for example, pepsin, bromelain, papain and the like which are obtained from animals, plants and bacterium.

The partial hydrolysis is conducted by dispersing soy protein into water, adjusting the pH and the temperature to the optimum pH and the temperature of the enzyme being used, and adding the enzyme subsequently.

The reaction time of partial hydrolysis should be long enough to hydrolyze soy protein with protease until two kinds of hydrolyzed products are formed wherein one is a low molecular weight part having high foaming capacity and wherein the other one is a high molecular weight part having high emulsifying capacity.

Namely, the former has the 5% TCA solubilization by weight of 70% or more, and the latter has the 5% TCA solubilization by weight of 10–40%. From a point of view of stability of the product, it is preferable to control the reaction time to within 20 hours.

The hydrolysis is terminated by inactivating the enzyme by heating at 75° C. for more than 5 minutes.

The hydrolyzed products thus obtained are separated into two parts which have the 5% TCA solubilizations by weight expected.

For this separation, by way of example, there can be employed the methods as follows:

The first method comprises adjusting the pH of the hydrolyzed solution to pH6.8–7.0, optionally removing insoluble matter, and adjusting the pH of the solution to pH2.5–5 to precipitate, then separating the supernatant and the precipitate by centrifugation. The pH of the solution at the separating operation by precipitating should be decided to be the optimum pH between pH2.5–5 to separate out the precipitate having the 5% TCA solubilization by weight of 10–40% from the supernatant having the 5% TCA solubilization by weight of 70% or more in its dried powdery state, paying attention to the time of hydrolysis. Contrary, to what would be expected when precipitating beyond this pH range, the hydrolyzed products having the expected solubilization rates can not be obtained.

Another method of separation comprises adjusting the pH of the solution to pH6.8–7.0, optionally removing insoluble matter, then subjecting the solution to ultrafiltration with an ultrafiltration membrane. The molecular weight cut off of the membrane is optimum at 15,000–20,000, although the conditions and the like vary according to the characteristics of the membrane being used.

Usually, treating the solution with a commercial ultrafiltration membrane of 15,000–20,000 molecular weight cut off, the filtrate passed through the membrane contains the hydrolyzed protein which has the 5% TCA solubilization by weight of 70% or more, and the residual solution after completing the filtration contains the hydrolyzed protein which has the 5% TCA solubilization by weight of 10–40%.

The thus obtained hydrolyzed proteins having the 5% TCA solubilization by weight of 10–40% and 70% or more are used as such solution, or used in a powdered state after being dried.

In accordance with this invention, the hydrolyzed soy protein having the 5% TCA solubilization by weight of 10–40% possesses high emulsifying capacity and excellent emulsifying stability, and the one having the 5% TCA solubilization by weight of 70% or more possesses high foaming capacity and excellent foaming stability.

A hydrolyzed soy protein having the 5% TCA solubilization by weight beyond the range of 10–40% lacks emulsifying capacity and can not work as an emulsifying agent. On the other hand, a hydrolyzed soy protein having the 5% TCA solubilization by weight less than 70% lacks good foaming capacity and can not work as foaming agent.

As is apparent from the above, this invention provides the process of partially hydrolyzing raw material of soy protein with a protease, simultaneously separating the hydrolyzed products into two parts which have emulsifying properties or foaming properties respectively using their solubilities by weight in 5% TCA as the guidance of separation, and the process may be conducted easily.

This invention may be further illustrated by the following non-limitative examples.

A 5% TCA solubilization by weight, emulsifying capacity, emulsifying stability, foaming capacity and foaming stability are defined as follows:

A 5% TCA Solubilization By Weight 2 g of a sample of protein powders treated with enzyme are dissolved with 48 g of water and 50 g of 10% aqueous TCA solution are added thereto and vibrated sufficiently. The resulting precipitates are centrifuged and then, 10 g of the supernatant solution are sampled. Nitrogen is measured in accordance with Kjeldahl method.

On the other hand, total nitrogen of the protein powder sample used is measured and the 5% TCA solubilization by weight is calculated by the following formula.

5% TCA Solubilization(wt %) =

Nitrogen in 10 g of the Supernatant × 10 (mg/Total Nitrogen in 2 g of the Sample (mg) × 100

Emulsifying capacity

Ag of sample solution which has 1% concentration of emulsifying agent is introduced into a 1 l beaker. Then soybean oil is added to the solution at the rate of 1 g/sec under stirring with Homomixer HV-M type (the trade name by Tokushukika Kogyo, Japan) at 14,000 rpm to a total amount of 400 g. After adding the oil, stirring is continued for an additional 5 minutes to emulsify.

The emulsifying capacity is represented by the weight (g) of the oil per 1 g of the sample solution at the upper limit when oil in water type emulsion can be formed varying the proportion of the oil to the sample solution.

$$\text{Emulsifying capacity} = \frac{400 - A}{\frac{A}{100}}$$

Emulsifying stability 510 g of a soybean oil is added to 300 g of 10% sample solution at the rate of 1 g/sec under stirring by a Robot Coupe R-4V type (trade name by T.K. Supplies Co., Ltd.) at 3,000 rpm. After adding the oil, stirring is continued for additional 5 minutes to emulsify. The emulsified substance thus obtained is tested on its emulsification state by heating at 120° C. for 15 minutes.

The emulsifying stability of the sample which does not separate into oil layer and aqueous layer by the above test is evaluated as good one.

Foaming capacity 200 ml of 1% sample solution of foaming agent is introduced into a cylinder (100 mm of inside diameter, 1,000 ml of volume), then it is stirred with Homomixer at 8,500 rpm for 1 minute to foam, followed by more 4 minutes stirring at 11,500 rpm.

The total volume A of the foaming sample is measured. The foaming capacity is represented by the A.

Foaming stability

The foaming sample is allowed to stand for 1 hour after measuring the foaming capacity as described above. Then, the total volume B of the sample is measured again.

The foaming stability is defined by the following equation.

$$\text{Foaming stability (\%)} = \frac{B}{A} \times 100$$

EXAMPLE 1

1 kg of soy protein isolate was dispersed in ten times amount of water, then the pH of the mixture was adjusted to pH7.0. 10 g of papain (by Novo Industry Incorporated) was added to the mixture, and hydrolysis of the protein was carried out for 6 hours. Then, the mixture was heated at 75° C. for 20 minutes to inactivate the protease. The dried content of the hydrolyzed solution had a 5% TCA solubilization rate of 63.8%.

The solution is acidified with HCl to pH3.0 to precipitate, then the mixture is subjected to centrifugation to separate the precipitate and the supernatant.

The precipitate separated above is dispersed in water, neutralized to pH6.8 with NaOH and freeze dried to obtain 540 g of the product (hereinafter refered to as "Hydrolyzed Protein I"). Hydrolyzed Protein I had a 5% TCA solubilization by weight of 30.2%.

The supernatant is neutralized to pH6.8 with NaOH too, and freeze dried to obtain 420 g the product (hereinafter referred to as "Hydrolyzed Protein II").

Hydrolyzed Protein II had a 5% TCA solubilization by weight of 80.4%. The emulsifying properties and the foaming properties of those hydrolyzed products are shown in Table I. Hydrolyzed Protein I possessed high emulsifying capacity of 360 as shown in the table, and excellent emulsifying stability. Hydrolyzed Protein II possesed high foaming capacity of 900 and excellent foaming stability of 79% respectively.

On the other hand, the emulsifying capacity of the control of hydrolyzed proteins having the 5% TCA solubilization by weight of 63.8% obtained by directly freeze drying the hydrolyzed solution before being separated was inferior to that of the example of this invention as it was 260, and the emulsifying stability was not good. The foaming capacity and the foaming stability of the control are inferior to those of the example as they were 580 and 60% respectively.

TABLE I

| 5% TCA Solubilization (wt %) | Control | Hydrolyzed Protein I | Hydrolyzed Protein II |
|---|---|---|---|
| emulsifying Properties | 63.8 | 30.2 | 80.4 |
| Emulsifying Capacity | | | |
| $\left(\frac{\text{g of soybean oil}}{\text{1g of sample}}\right)$ | 260 | 360 | No emulsification |
| Emulsifying Stability | Not good | Good | — |
| Foaming Properties | | | |
| Foaming Capacity (ml) | 580 | 400 | 900 |
| Foaming | 60 | 54 | 79 |

TABLE I-continued

| 5% TCA Solubilization (wt %) | Control | Hydrolyzed Protein I | Hydrolyzed Protein II |
|---|---|---|---|
| Stability (%) | | | |

EXAMPLE 2

Defatted soy flour was dispersed in ten times weight of water, then the pH of the mixture was adjusted to pH7.0. The mixture was heated at 50° C. under stirring for 30 minutes, then insoluble substance was rejected with centrifugation.

Ethanol was added to the aqueous supernatant until 65%(w/w) alcoholic concentration to precipitate protein. The precipitate protein was separated from the mixture by centrifugation and dried. 500 g of the dried protein was dispersed in twenty times weight of water and acidified to pH1.8 by HCl. 2 g of pepsin (by Amano Pharmaceutical Co., Ltd.) was added to the mixture, then hydrolysis was conducted at 55° C. for 4 hours. Then the mixture was heated at 75° C. for 20 minutes to inactivate enzymes. The hydrolyzed solution was neutralized to pH6.8 by NaOH and subjected to separation with an ultrafiltration membrane. An ultrafiltration membrane (IRIS3038 by Rhône-Poulenc Co., Ltd.) whose molecular weight cut off is 15,000-20,000 was used for this separation.

After this filtration, the residual solution was freeze dried to obtain 220 g of product (hereinafter referred to as Hydrolyzed Protein III) having the 5% TCA solubilization by weight of 20.7%. The filtrate was freeze dried to obtain 230 g of product (hereinafter referred to as Hydrolyzed Protein IV) having the 5% TCA solubilization by weight of 86.1%.

The emulsifying properties and the foaming properties of the hydrolyzed products thus obtained are shown in Table II. Hydrolyzed Protein III possessed high emulsifying capacity of 340 as shown in the table and excellent emulsifying stability. Hydrolyzed Protein IV possessed high foaming capacity of 980 and excellent foaming stability of 86% respectively.

TABLE II

| | | Hydrolyzed Protein III | Hydrolyzed Protein IV |
|---|---|---|---|
| 5% TCA Solubilization (wt %) | | 20.7 | 86.1 |
| emulsifying Properties | Emulsifying Capacity g of soybean oil 1 g of sample | 340 | No emulsification |
| | Emulsifying Stability | Good | — |
| Foaming Properties | Foaming Capacity (ml) | 420 | 980 |
| | Foaming Stability (%) | 52 | 86 |

What is claimed is:

1. A process for preparing hydrolyzed products of soy protein which comprises
   (a) partially hydrolyzing soy protein with a protease to obtain a solution containing two parts of said hydrolyzed products having differing solubilities in 5% trichloroacetic acid aqueous solution, wherein one of said two parts has a solubility of 10-40% by weight in 5% trichloroacetic acid and the other of said two parts has a solubility of 70% or more by weight in 5% trichloroacetic acid, and
   (b) separating said two parts from each other by steps consisting essentially of neutralizing the solution containing two parts of said hydrolyzed products to pH 6.8-7.0, removing insoluble matter from said solution, and separating said hydrolyzed products into said two parts with an ultrafiltration membrane.

2. A process for preparing hydrolyzed products of soy protein which comprises
   (a) partially hydrolyzing soy protein with a protease to obtain a solution containing two parts of said hydrolyzed products having differing solubilities in 5% trichloroacetic acid aqueous solution, wherein one of said two parts has a solubility of 10-40% by weight in 5% trichloroacetic acid and the other of said two parts has a solubility of 70% or more by weight in 5% trichloroacetic acid, and
   (b) separating said two parts from each other by steps consisting essentially of neutralizing the solution containing two parts of said hydrolyzed products to pH 6.8-7.0, removing insoluble matter from said solution, precipitating one of said two parts of said hydrolyzed products by acidifying said solution to pH 2.5-5 to form a supernatant and precipitate, and separating the supernatant and the precipitate.

3. The process of claim 1 wherein the molecular weight cut off of the ultrafiltration membrane is 15,000-20,000.

4. The process of claim 1 which comprises heating the soy protein or precipitating the soy protein with alcohol before hydrolysis.

5. The process of claim 1 wherein the protease is obtained from an animal, a plant or a bacterium.

6. The process of claim 5 wherein the protease is papain.

7. The process of claim 5 wherein the protease is pepsin.

8. The process of claim 2 which comprises heating the soy protein or precipitating the soy protein with alcohol before hydrolysis.

9. The process of claim 3 which comprises heating the soy protein or precipitating the soy protein with alcohol before hydrolysis.

10. The process of claim 2 wherein the protease is obtained from an animal, a plant or a bacterium.

11. The process of claim 10 wherein the protease is papain.

12. The process of claim 10 wherein the protease is pepsin.

13. The process of claim 3 wherein the protease is obtained from an animal, a plant or a bacterium.

14. The process of claim 13 wherein the protease is papain.

15. The process of claim 13 wherein the protease is pepsin.

16. The process of claim 4 wherein the protease is obtained from an animal, a plant or a bacterium.

17. The process of claim 16 wherein the protease is papain.

18. The process of claim 16 wherein the protease is pepsin.

* * * * *